United States Patent [19]

Drysdale et al.

[11] Patent Number: 4,952,291

[45] Date of Patent: Aug. 28, 1990

[54] PROCESS FOR THE PURIFICATION OF ALDEHYDES

[75] Inventors: Neville E. Drysdale, Newark, Del.; Frederick W. Mader, Kennett Square, Pa.; Rudolf E. Svadlenak, Hockessin, Del.

[73] Assignee: E. I. Du Pont de Nemours and Company, Wilmington, Del.

[21] Appl. No.: 446,775

[22] Filed: Dec. 6, 1989

[51] Int. Cl.$^5$ .............................................. B01J 19/08
[52] U.S. Cl. ........................... 204/157.93; 204/158.21; 210/689; 210/690; 210/748
[58] Field of Search ...................... 204/157.93, 158.21; 210/748, 689, 690

[56] References Cited

U.S. PATENT DOCUMENTS 4,356,071 10/1982 Fenton ................................. 528/232
4,502,923 3/1985 Dryoff ................................. 560/177

*Primary Examiner*—John F. Niebling
*Assistant Examiner*—Ben C. Hsing
*Attorney, Agent, or Firm*—Charles E. Krukiel

[57] ABSTRACT

An aldehyde in a mixture containing hemiacetals and hydrates of the aldehyde is purified by treating the mixture with an effective amount of microwave radiation to decompose the hemiacetals and hydrates. Liberated water and/or alcohol is immediately removed with an adsorbent.

28 Claims, No Drawings

PROCESS FOR THE PURIFICATION OF ALDEHYDES

BACKGROUND OF THE INVENTION

This invention relates in general to a process for purifying an aldehyde and, more particularly, to a method of purifying an alkyl glyoxylate by decomposing its hemiacetals and hydrates and removing the liberated water and/or alcohol.

High purity alkyl glyoxylates are important in the synthesis of pharmaceuticals and various polymers. In order to manufacture long-chained polyacetals, i.e., polyacetals with molecular weights of at least 8800, the water and alcohol content (expressed as monomeric species) of the aldehyde must be low, i.e., usually less than 1000 ppm (w/w). The maximum chain length of the polyacetal is approximately equal to the molar ratio of the aldehyde to water plus alcohol, all expressed as monomeric species.

Alkyl glyoxylates can be produced by the oxidative dehydrogenation of alkyl glycolates in the presence of a silver catalyst. For each mole of glyoxylate produced, about one mole of water is co-produced, along with lesser amounts of the alcohol corresponding to the alkyl glyoxylate and various other minor by-products, i.e., glyoxylic acid. Product isolation to the above purity levels by separation processes such as distillation is complicated by reactions between the alkyl glyoxylate and hydroxylic species such as water and the alcohol corresponding to the alkyl glycolate.

Kinetic studies show that the equilibrium constants for the hydrate and hemiacetal formation are large. Thus, alkyl glyoxylate containing small amounts of water and alcohol is difficult to purify, since the water is tied up as the hydrate, and the alcohol is tied up as the hemiacetal. Therefore, separation of any hydroxyl group from the alkyl glyoxylate cannot be achieved by simple distillation and/or inert gas stripping.

U.S. Pat. No. 4,502,923 discloses a method of isolating alkyl glyoxylate from its impurities in a series of distillations. First, the water and alcohol content is lowered by vacuum distillation in a first column. The residue from the first column is distilled in a second vacuum column to decrease the ratio of alkyl glycolate to alkyl glyoxylate. The residue from the second column is then distilled in a third column at a higher pressure to recover the high purity alkyl glyoxylate as an intermediate distillate. A low boiling azeotroping agent, such as methylene chloride, is introduced to cause water and alcohol to distill overhead. In order to produce high purity alkyl glyoxylate, it is necessary to have a large recycle stream on the order of 11 lbs. of recycle alkyl glycolate throughout the three distillation columns per pound of product alkyl glyoxylate takeoff. In this scheme, the capital investment in plant equipment is high, energy consumption is high, and the production of product is relatively low.

Australian Patent No. 30007-84 discloses a method for isolation of the glyoxylic ester from materials co-formed during the oxidative dehydrogenation of an alkyl glycolate. Immediately after leaving the reactor, the gaseous reaction mixture is quenched with a low-boiling entrainer, such as a hydrocarbon having a lower boiling point than the glyoxylic ester. The entrainer is used to azeotropically distill water and alcohol. The reaction mixture, along with the entrainer, are passed to a rectifying column, where the water azeotrope and other low boilers are taken overhead while the glyoxylic ester is taken off as bottoms. Some of the water and alcohol in the reaction mixture forms high-boiling hemiacetals and hydrates before they can be azeotropically distilled. Consequently, additional steps are required to obtain high purity alkyl glyoxylate.

It is known that high purity alkyl glyoxylate can be isolated from a mixture containing alkyl glyoxylate, water, and alcohol in combined form by distillation from $P_2O_5$ (W. Oroshnik and P.E. Spoerri, J. Amer. Chem. Soc. 1941, 63,3338). Product losses are high and a highly corrosive waste stream is formed which poses difficult disposal problems. In addition, the reaction with $P_2O_5$ is extremely exothermic. Consequently, this technique is suitable only for small-scale operations.

U.S. Pat. No. 4,356,071 discusses treating anhydrous trioxane or formaldehyde with microwave radiation prior to polymerization to form thermally stable polymers. This process is not directed toward product purification.

The above-described methods of product purification are uneconomical, due to the high cost of multiple distillation stages, high product losses and, in the case of treatment with $P_2O_5$, the additional problem of disposal of corrosive waste. It would be desirable to have an economical method of product purification which decomposes the hemiacetal byproducts to increase product yield. It is also desirable to have a more efficient method for producing high purity alkyl glyoxylate with a low water content Such an economical process would involve the removal of water and alcohols and thus prevent the formation of hemiacetals and hydrates.

SUMMARY OF THE INVENTION

A process is provided for purifying an aldehyde in a mixture which contains hemiacetals and hydrates of the aldehyde, which comprises treating the mixture with an effective amount of microwave radiation to decompose hemiacetals and hydrates and immediately removing liberated water and/or alcohol from the solution with an absorbent. A molecular sieve can be used to absorb freed water and/or alcohol. In a preferred aspect of the present invention, the solution containing a solvent is subjected to microwave radiation at frequencies of from about 1000-3000 MHz for a period sufficient to decompose any hemiacetals and hydrates. Any liberated water and alcohol is immediately removed from the solution by a molecular sieve absorbent.

This process is also applicable to the purification of alkyl glyoxylates in a solution containing the reaction products from the catalytic gas phase oxidative dehydrogenation of alkyl glycolates. The solution, which may contain a solvent such as nitrobenzene, for example, is in contact with a bed of molecular sieves while being subjected to microwave radiation. The molecular sieves remove the water and/or alcohol liberated by the decomposition of hemiacetals and/or hydrates in the solution.

DETAILED DESCRIPTION OF THE INVENTION

According to the present invention, an aldehyde in a mixture can be purified by decomposing its hemiacetals and hydrates with microwave radiation to liberate water and/or alcohol. The liberated water and/or alcohol is immediately removed from the mixture by an absorbent material to prevent the reformation of the hemiacetals and hydrates. The present invention is particularly useful for purifying a mixture containing alkyl glyoxylate, its hemiacetals, and hydrates. The mixtures or solutions of alkyl glyoxylate described herein are obtained by the oxidative dehydrogenation of the corresponding alkyl glycolate. The composition of these solutions is described herein as if only monomeric species exist therein, but the previously described hemiacetal and hydrate reactions do, in fact, occur, and the hemiacetals and hydrates are present in the reaction mixture.

The present invention is useful for all alkyl moieties of the alkyl glyoxylate. It is particularly suitable for alkyl moieties containing from 1-6 carbon atoms. The effect of the microwave radiation on the hemiacetals and hydrates of the alkyl glyoxylate in the mixture is known by observing a sharp reduction in the amount of alcohol and water found in the alkyl glyoxylate as a result of such treatment. In processes conducted according to the present invention, the microwave treatment has no detrimental effect on the alkyl glyoxylate product.

The term "microwave radiation" as used herein is defined in Van Norstrand's Scientific Encyclopedia, 1958, as extending from 1,000 MHz to 300,000 MHz. Although any microwave frequencies may be used in the process of the present invention, microwave frequencies between 1000 and 4000 MHz are preferred. In a preferred embodiment, microwave frequencies of about 2,450 MHz are desirably used.

In a preferred embodiment, the alkyl glyoxylate being purified contains impurities from the reaction products of the catalytic gas phase oxidative dehydrogenation of an alkyl glycolate. The amount of water and/or alcohol in the solution preferably ranges from a trace to about 3 percent by weight, more preferably, from about 0.1 to 1.0 weight percent for optimal removal of water and/or alcohol. The reaction mixture can be dissolved in part in a solvent. The resulting solution preferably contains from about 10% to 80%, more preferable from about 40% to 60% of the solvent. Preferred solvents are water immiscible, such as aryl aromatics, e.g., nitrobenzene.

It is preferred, but not critical, that the microwave treatment of the present invention be carried out in an inert atmosphere. Any atmospheric inert gas is suitable, but most preferred are nitrogen and the noble gases, such as argon, and helium.

The microwave treatment of the reaction mass must be carried out for an effective length of time. The length of the microwave treatment will depend upon the amount and/or concentration of hemiacetals and/or hydrates present in the solution being treated, the power level of the microwave source and the frequency of the microwave radiation. The greater the concentration of hemiacetals and hydrates in the mixture, the longer the exposure time needed to decompose the hemiacetals and/or hydrates at a given power level. Normally, the microwave treatment is carried out for a period ranging from about 15 seconds to 5 minutes, but shorter or longer treatment periods may be used. When there is only a trace amount of hemiacetals and/or hydrates, periods from about 15-30 seconds may be sufficient. Microwave radiation at any desired power level can be used.

In a preferred embodiment, a bed of absorbent material is continuously subjected to microwave radiation while a stream of the liquid alkyl glyoxylate mixture flows through the bed. The bed of absorbent is contained in a column constructed of material permeable to microwave radiation. The microwave treatment of the present invention can be carried out in any appropriate type of container or column which is transparent or semitransparent to microwave radiation. Suitable materials of construction are quartz glass and non-metallic ceramics.

Water and/or alcohol liberated by the decomposition of hemiacetals and hydrates present in the solution are removed by an absorbent material. The resultant dried solution containing alkyl glyoxylate product can be collected in a receiver at the bottom of the column. Although any type of suitable absorbent material may be used, it is preferred to use an absorbent such as a high capacity molecular sieve. The molecular sieve is preferably in the form of pellets or beads. Preferred are the molecular sieves of Type 5A. It was found that equally good results are obtained with 1/16" cylindrical 5A sieves from Linde and spherical 5A sieves from EM Science. Any type of absorbent may be used as long as it is not deleteriously affected by the microwave treatment and otherwise remains effective during the treatment to remove liberated water and/or alcohol.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents, and publications, if any, cited above and below are hereby incorporated by reference.

EXAMPLES

The solutions used in Examples 1-4 were obtained by the oxidative dehydrogenation of methyl glycolate. Part of the reaction mixture was then dissolved in nitrobenzene. The compositions are described as if only monomeric species are present, but the reactions described previously hold true in the examples.

EXAMPLE 1

A solution containing methyl glyoxylate and nitrobenzene at ambient temperature and pressure was introduced at a rate of 2.4 cc/min into a glass column filled with Type 5A 1/16" Linde molecular sieve and under a nitrogen atmosphere. The composition of the original solution in weight percent is shown in Table 1, below. The bed volume was 10.8 ml. 648 watts of microwave radiation at a frequency of 2450 MHz were used to irradiate the column. The composition of the resulting solution after the microwave treatment is also shown. Exit temperatures of the solution after the microwave treatment ranged from 81° to 100° C. 100% of the water was removed with virtually no destruction of the methyl glyoxylate.

TABLE 1

| Component | % before microwave treatment | % after microwave treatment | loss % |
|---|---|---|---|
| water | 0.423 | n.d. | 100 |

TABLE 1-continued

| Component | % before microwave treatment | % after microwave treatment | loss % |
|---|---|---|---|
| methanol | 0.497 | 0.433 | 13 |
| methyl glyoxylate | 21.1 | 21.4 | — |
| methyl glycolate | 16.2 | 16.4 | — |
| nitrobenzene | 61.4 | 61.4 | — | n.d. = none detected

COMPARATIVE EXAMPLE 2

When the molecular sieves were bathed in a solution of methyl glyoxylate and nitrobenzene at ambient temperature (24° C.), results similar to the steam experiment of Example 3 were obtained. The experiment was carried out using an air atmosphere in a column containing 10.8 ml of bed volume. The results are shown in Table 2.

TABLE 2

| Component | % before sieves | % after sieves | loss % |
|---|---|---|---|
| water | 0.581 | 0.446 | 23 |
| methanol | 1.170 | 1.175 | — |
| methyl glyoxylate | 17.9 | 17.8 | — |
| methyl glycolate | 12.5 | 12.5 | — |
| nitrobenzene | 66.2 | 66.4 | — |

COMPARATIVE EXAMPLE 3

A run very similar to Example 1 was conducted with thermal energy supplied by steam (100° C.) in lieu of microwave energy to the same column as in the first example. The composition before and after the thermal treatment in weight percent is shown in Table 3. Thermal energy removed substantially less water than the microwave treatment of Example 1. Also, temperature increase by thermal energy alone did not increase water removal compared to Example 2 run at ambient temperature. The experiment was carried out in the presence of air. A Linde-type 5A sieve was used to absorb the freed water.

TABLE 3

| Component | % before steam treatment | % after steam treatment | loss % |
|---|---|---|---|
| water | 0.411 | 0.315 | 23 |
| methanol | 1.188 | 1.091 | 8.2 |
| methyl glyoxylate | 17.7 | 17.6 | — |
| methyl glycolate | 12.5 | 12.5 | — |
| nitrobenzene | 66.7 | 66.7 | — |

EXAMPLE 4

12 g of a solution containing methyl glyoxylate and nitrobenzene was added to 12 g of Linde-type 5A molecular sieves in a capped glass jar with a bed volume of 17 ml. The jar was placed in a 700 watt microwave oven and exposed for 30 seconds at a 10% power power level at a frequency of 2450 MHz. The final temperature of the mixture reached 59° C. The solution was then immediately analyzed.

In a comparative experiment, 12 g of an untreated sample of the same solution used in the first experiment was heated to approximately 59° C. in a thermal oven and 12 g of the same molecular sieve were added. After 30 seconds, a sample was taken and analyzed. Considerably less water was removed by thermal treatment than by microwave treatment. The results of these experiments are shown in Table 4.

TABLE 4

| Component | % before treatment | % after microwave treatment | loss % | % after thermal treatment | loss % |
|---|---|---|---|---|---|
| water | 0.597 | 0.045 | 92 | 0.362 | 39 |
| methanol | 1.446 | 1.369 | 5.3 | 1.404 | 2.9 |
| methyl glyoxylate | 20.12 | 20.2 | — | 20.3 | — |
| methyl glycolate | 13.4 | 13.4 | — | 13.5 | — |
| nitrobenzene | 62.7 | 63.3 | — | 62.8 | — |

COMPARATIVE EXAMPLE 5

In this example, methanol is removed from a methanol/methyl glyoxylate reaction product using thermal heating to decompose the methyl hemiacetal.

A 100-ml Erlenmeyer flask was charged with methanol (1.01 g, 0.032 mole), and methyl glyoxylate (11.5 g, 0.126 mole) was distilled into the flask. When the exotherm from formation of the methyl hemiacetal abated, nitrobenzene (21.5 g) was added as solvent, followed by 5A molecular sieve (14.96 g). The mixture was heated to 110° C. and samples periodically withdrawn for analysis of methanol content by gas chromatography. The data in Table 5 illustrates that complete removal of methanol required only slightly more than 120 minutes.

TABLE 5

| Time (min) | Methanol (moles) |
|---|---|
| 0 | 0.032 |
| 15 | 0.028 |
| 30 | 0.009 |
| 45 | 0.006 |
| 60 | 0.005 |
| 120 | 0.003 |

EXAMPLE 6

This example illustrates the removal of methanol from a methanol/methyl glyoxylate reaction product using microwaves to accelerate decomposition of the methyl hemiacetal.

A 100 ml Erlenmeyer flask was charged with methanol (1.01 g, 0.032 mole), and methyl glyoxylate (10.45 g, 0.119 mole) was distilled into the flask. When the exotherm from formation of the methyl hemiacetal abated, nitrobenzene (20.9 g) was added as solvent followed by 5A molecular sieves (15.01 g). The mixture was placed in an Amana Model RS485P microwave oven and irradiated at 10% power level at a frequency of 2450 MHz. Samples were withdrawn at one-minute intervals and analyzed for methanol content by gas chromatography. The data in Table 6 demonstrates that methanol removal was complete in 5 minutes.

TABLE 6

| Time (min) | Methanol (moles) |
|---|---|
| 0 | 0.032 |

TABLE 6-continued

| Time (min) | Methanol (moles) |
|---|---|
| 1 | 0.030 |
| 2 | 0.027 |
| 3 | 0.011 |
| 4 | 0.002 |
| 5 | 0.000 |

Thus, while it took less than 4 minutes to remove < 90% of the methanol in this experiment, it took about 120 minutes to do so when the energy was thermally supplied, as in Example 5.

The preceding examples can be repeated with similar success by substituting the specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for purifying an aldehyde in a mixture which contains hemiacetals and hydrates of the aldehyde wherein the hemiacetals and hydrates are decomposed and liberated water and alcohol are removed, comprising the steps of:
   (a) treating the mixture with an effective amount of microwave radiation to decompose hemiacetals and hydrates, and
   (b) immediately removing liberated water and alcohol from the mixture with an absorbent.

2. The process of claim 1, wherein the absorbent in step (b) is a molecular sieve.

3. The process of claim 1, wherein the mixture is subjected to the microwave radiation while in contact with the absorbent.

4. The process of claim 3, wherein the microwave radiation is at frequencies of from about 1,000-300,000 MHz.

5. The process of claim 4, wherein the mixture is subjected to microwave radiation for a period of from about 15 seconds to 5 minutes.

6. The process of claim 1, wherein the mixture contains a solvent for the aldehyde.

7. The process of claim 6, wherein the process is carried out in an inert atmosphere.

8. The process of claim 1, wherein the aldehyde is methyl glyoxylate.

9. The process of claim 8, wherein the absorbent in step (b) is a molecular sieve, wherein the mixture is subjected to microwave radiation while in contact with the absorbent, wherein the process is carried out in an inert atmosphere, and wherein the mixture is subjected to microwave radiation for a period from about 15 seconds to 5 minutes, wherein the microwave radiation is at a frequency from about 1000-300,000 MHz, and the mixture contains a solvent for the methyl glyoxylate.

10. In a process for purifying an alkyl glyoxylate in a mixture containing reaction products from the catalytic gas phase oxidative dehydrogenation of an alkyl glycolate wherein hemiacetals and hydrates are decomposed and liberated water and alcohol are removed, the improvement which comprises the steps of:
   (a) subjecting the solution to an amount of microwave radiation effective to decompose hemiacetals and hydrates in the solution, and
   (b) immediately removing liberated water and alcohol from the mixture with an absorbent.

11. The process of claim 10, wherein the absorbent in step (b) is a molecular sieve.

12. The process of claim 10, wherein the mixture contains a solvent for the alkyl glyoxylate.

13. The process of claim 10, wherein the mixture contains from < 0.01 to 3.0% by weight of water.

14. The process of claim 10, wherein the mixture is subjected to microwave radiation at a frequency of from about 1,000-300,000 MHz.

15. The process of claim 14, wherein the mixture is in contact with the molecular sieve while being subjected to the microwave radiation.

16. The process of claim 15, wherein the mixture is irradiated for a period of from 15 seconds to about 5 minutes.

17. The process of claim 10, wherein the radiation treatment is carried out in an inert atmosphere.

18. The process of claim 10, wherein the inert atmosphere is nitrogen.

19. In a process for purifying an alkyl glyoxylate in a solution containing reaction products from the catalyzed gas phase oxidative dehydrogenation of an alkyl glycolate, the improvement which comprises:
   subjecting the solution to microwave radiation at a frequency of from about 1000-300,000 MHz for a period of time sufficient to decompose hemiacetals and hydrates, while the solution is in contact with a bed of a molecular sieve effective to absorb liberated water and alcohol from the solution.

20. The process of claim 19, wherein the solution contains a solvent for the alkyl glyoxylate.

21. The process of claim 20, wherein the solvent is nitrobenzene.

22. The process of claim 21, wherein the amount of water in the mixture is from about 0.1 to 1.0 weight percent and the alkyl glyoxylate is methyl glyoxylate.

23. The process of claim 19, wherein the bed of molecular sieves is irradiated while the solution is flowing through the bed.

24. The process of claim 19, wherein the molecular sieve is Type 5A.

25. The process of claim 19, wherein the process is carried out in a nitrogen atmosphere.

26. The process of claim 19, wherein the alkyl glyoxylate is methyl glyoxylate.

27. In a process for purifying methyl glyoxylate in a solution containing reaction products from the catalyzed gas phase oxidative dehydrogenation of methyl glycolate, the improvement comprises: passing a solution of the methyl glyoxylate comprising hemiacetals and hydrates thereof in nitrobenzene through a bed of Type 5A molecular sieve in a nitrogen atmosphere while subjecting the bed to microwave radiation at a frequency of from about 1000300,000 MHz for a period of time sufficient to decompose the hemiacetals and hydrates, the bed being effective to absorb from the solution the water and alcohol liberated by the decomposition of the hemiacetals and hydrates.

28. The process of claim 27, wherein the starting nitrobenzene solution is the reaction product obtained by the catalytic dehydrogenation of methyl glycolate.

* * * * *